United States Patent [19]

Brunel

[11] Patent Number: 5,207,646
[45] Date of Patent: May 4, 1993

[54] SINGLE USE SHIELDABLE HYPODERMIC SYRINGE WITH A REUSABLE HANDLE

[76] Inventor: Marc Brunel, 64 Allees de Barcelone, 31000 Toulouse, France

[21] Appl. No.: 709,661

[22] Filed: Nov. 29, 1990

[51] Int. Cl.$^5$ .............................................. A61M 5/00
[52] U.S. Cl. ..................... 604/110; 604/197; 604/198; 604/232
[58] Field of Search ............... 604/110, 162, 171, 197, 604/198, 263, 232, 234

[56] References Cited

U.S. PATENT DOCUMENTS

| | | | |
|---|---|---|---|
| 2,571,653 | 10/1951 | Bastien . | |
| 2,925,083 | 2/1960 | Craig . | |
| 3,112,747 | 12/1963 | Cowley | 604/197 |
| 4,631,057 | 12/1986 | Mitchell | 604/198 |
| 4,642,103 | 2/1987 | Gettig | 604/234 |
| 4,702,738 | 10/1987 | Spencer | 604/198 |
| 4,747,829 | 5/1988 | Jacob et al. | 604/110 |
| 4,752,290 | 6/1988 | Schramm | 604/198 |
| 4,801,295 | 1/1989 | Spencer | 604/198 |
| 4,840,619 | 6/1989 | Hughes | 604/198 |
| 4,997,422 | 3/1991 | Chow et al. | 604/263 |
| 5,045,066 | 9/1991 | Scheuble et al. | 604/232 |
| 5,053,018 | 10/1991 | Talom et al. | 604/263 |
| 5,057,088 | 10/1991 | Narayanan et al. | 604/198 |
| 5,067,945 | 11/1991 | Ryan et al. | 604/263 |
| 5,084,030 | 1/1992 | Byrne et al. | 604/110 |
| 5,086,780 | 2/1992 | Schmitt | 604/198 |
| 5,120,309 | 6/1992 | Watts | 604/198 |

FOREIGN PATENT DOCUMENTS 0288003 4/1988 European pat. Off. .

Primary Examiner—C. Fred Rosenbaum
Assistant Examiner—Ronald K. Stright, Jr.
Attorney, Agent, or Firm—Auslander & Thomas

[57] ABSTRACT

A single use syringe comprises a separable, reusable handle including a piston (6) and a support part (2, 3) for a sleeve (4) having an interlocking structure (5) through which the piston (6) extends. The syringe body (11) has a tubular end (16) with an interlocking structure cooperating with that of the sleeve (4) of the handle (1) and the shape of which is adapted to interlock with said sleeve, and a protecting shell (12) having a locking section (22) capable of covering the tubular end (16) and the sleeve (4) so that they are locked in their interlocking position, said protective shell (12) being adapted for sliding along the syringe body (11) between two extreme positions, i.e. a forward position where it totally covers the injection needle and a pulled back position where it frees it and covers the interlocked tubular end (16) and sleeve (4).

27 Claims, 6 Drawing Sheets

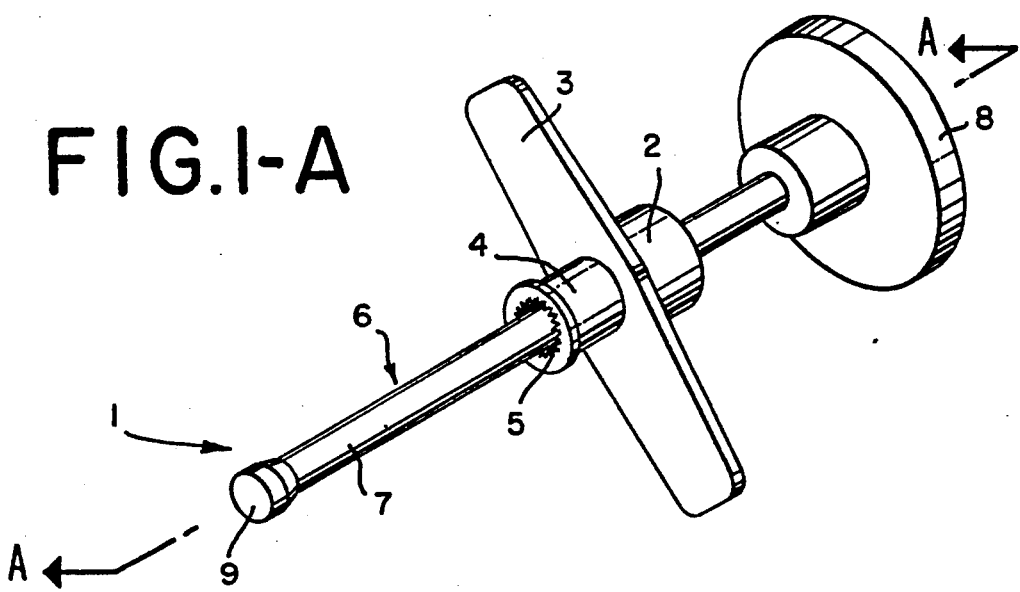
FIG.1-A
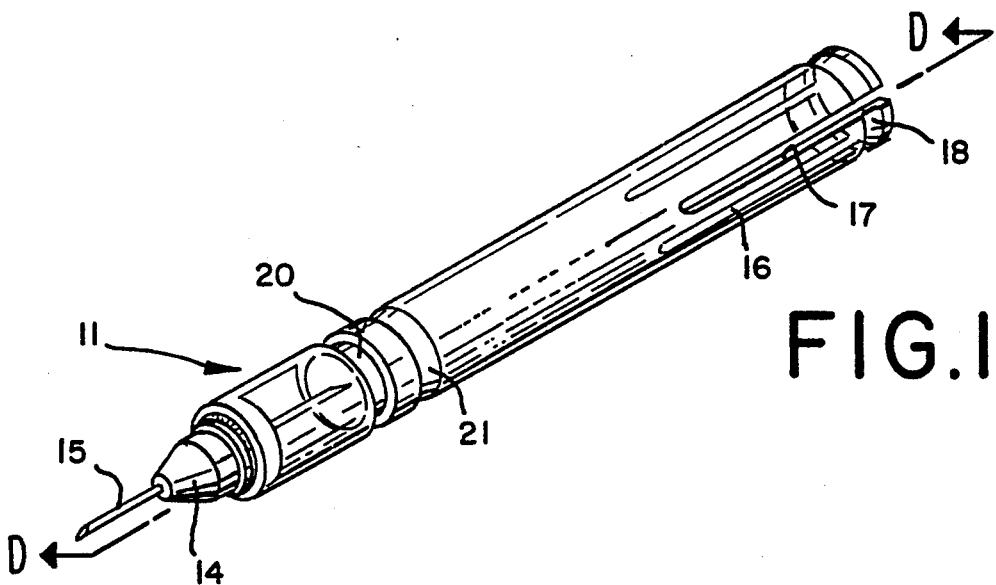
FIG.1-B
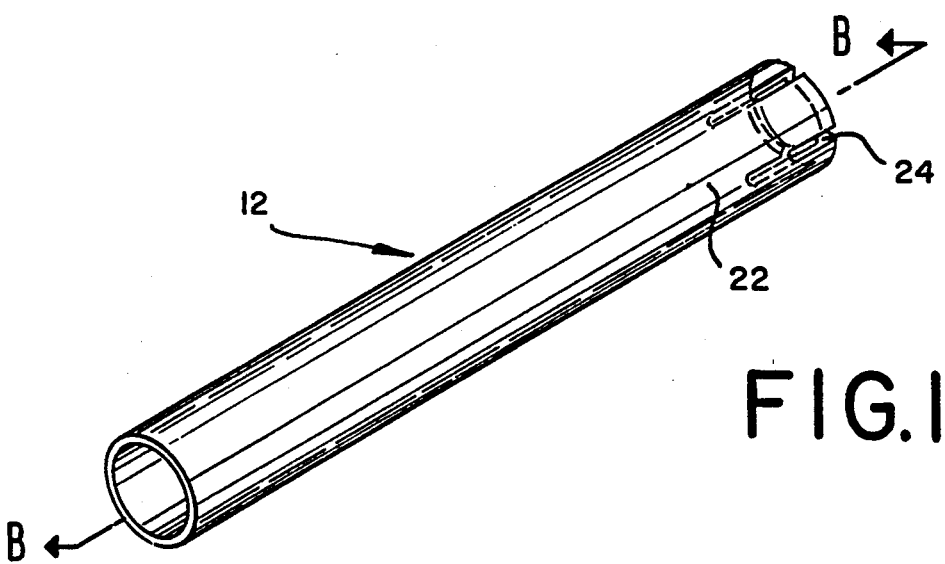
FIG.1-C

FIG.6
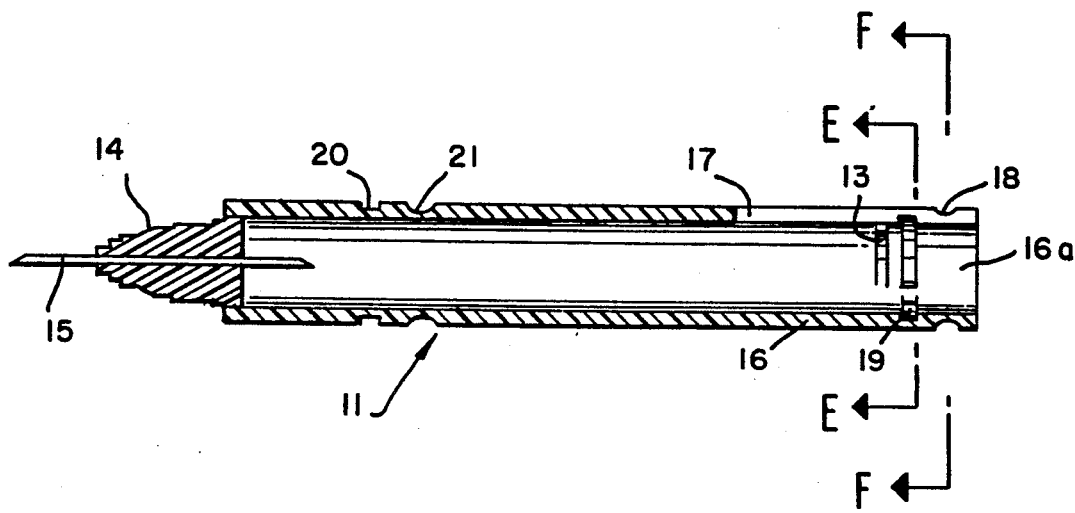
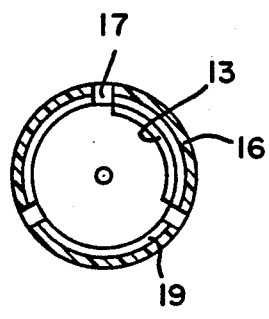
FIG.7
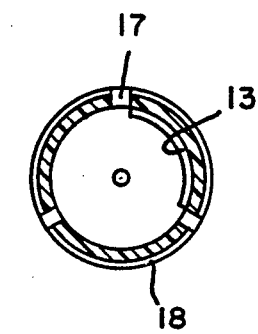
FIG.8

FIG.9
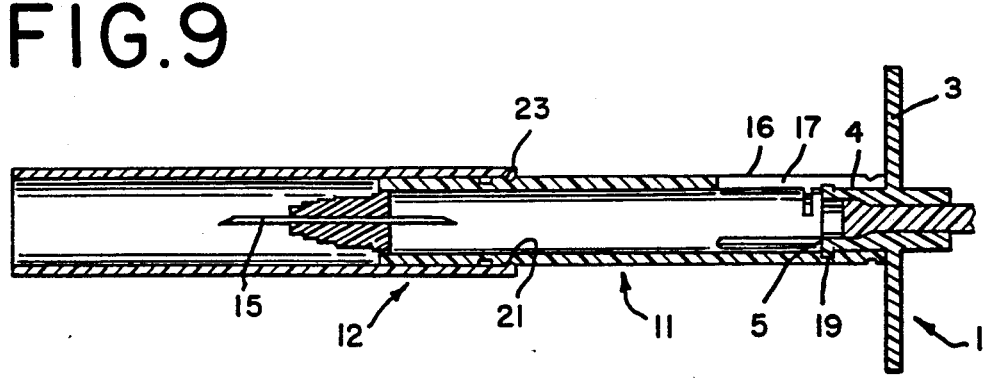
FIG.10
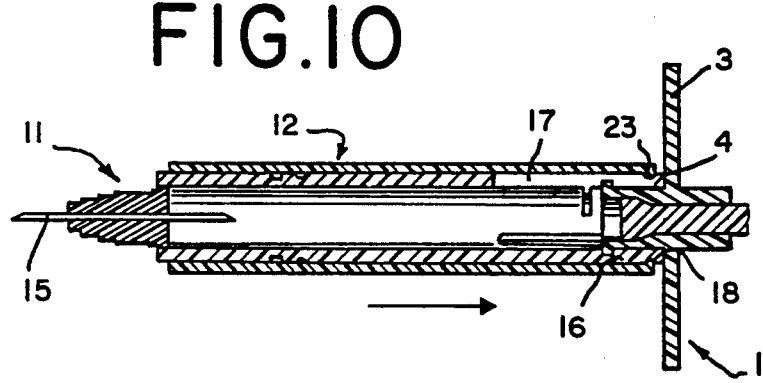
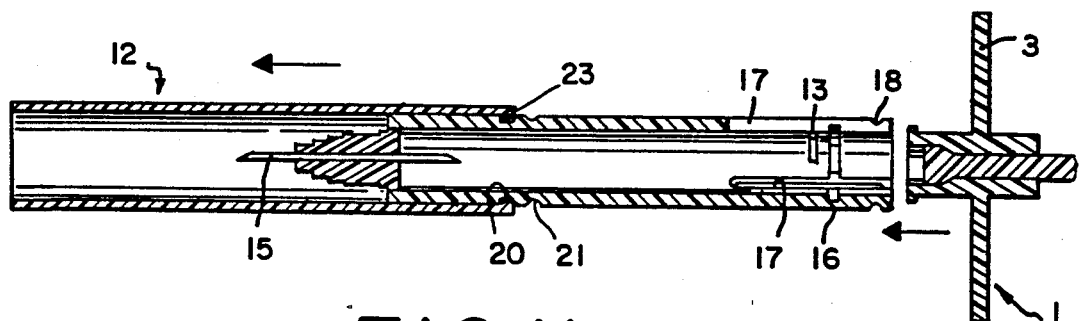
FIG.11

SINGLE USE SHIELDABLE HYPODERMIC SYRINGE WITH A REUSABLE HANDLE

BACKGROUND OF THE INVENTION

The invention relates to a syringe of the type having an injection needle for single use, notably for dentistry.

The classic syringes used in dentistry have a handle provided with a plunger and finger grip ribs and a syringe body able to be screwed removably onto this handle after a cartridge has been put in place. This body has further a threaded nose for the screwing on of a base carrying a needle, initially packaged in a protective case so as to avoid all risk of pricking when handling this needle and when screwing the base onto the syringe body. The case having been removed for use of the syringe is then put back in place for the unscrewing of the base. This type of syringe has four major disadvantages. Firstly, when the needle is capped again, the case will be opposite the end of the needle and accidents of pricking are relatively frequent with all the risks that pricking with a dirty needle involves. Furthermore, the syringe body intended to be reused is soiled by the patient's saliva, necessitating complete sterilization of this body after use. Besides, the cartridge is not protected during oral injection, despite the risks of accidental bursting thereof, due to the high pressures necessary for the injection of the liquid. Lastly, the operations of screwing and unscrewing, on the one hand of the base on the syringe body, and on the other hand, of the syringe body on the handle, are operations that take the practitioner relatively long.

DESCRIPTION OF THE RELATED ART

In a field other than dentistry, there are also syringes designed so as to remedy some of the above-mentioned disadvantages. These syringes, such as described in U.S. Pat. No. 4,702,738, have a syringe body and a handle in one piece and a protective case able to slide externally along the syringe body between a rear position where the needle is exposed and a forward position where this case covers the needle entirely. These syringes thus remedy the first three deficiencies mentioned above of the classic dental syringes. However, due to their design, they require discarding the entire syringe after use. Moreover, such a syringe modified to adapt it to dentistry does not solve the problems posed by the times for assembly and disassembly of the various elements.

SUMMARY OF THE INVENTION

The present invention aims to remedy the disadvantages of the known syringes and its object is to provide a syringe having an injection needle for single use, of very simple design, eliminating all risk of pricking with this needle, before and after use, and the assembly and disassembly of which require very quick and easy operations.

Another object is to supply a syringe whose body can be packaged under sterile wrapping.

Another object is to supply a syringe protecting the patient against all risk of bursting of the cartridge, while permitting visualization of the liquid level in the cartridge.

Another object is to furnish a syringe preventing any subsequent re-use of the cartridge.

To this effect, the invention covers a syringe of the type having an injection needle for single use, notably for dentistry, and comprising:

a syringe handle with a plunger and a support piece traversed by said plunger and movable along the latter, a syringe body provided at one of its ends with a base carrying the injection needle so as to define an active injection portion, means for removable attachment of the syringe body on the syringe handle, and a protective case of a form adapted to house the needle and its base.

According to this invention, this syringe is characterized in that the means of removable attachment of the syringe body on the handle comprise:

a tubular adapter ["ferrule"] carried by the syringe body opposite the base, and provided with a fitting [interlocking] structure, a sleeve integral with the support piece of the handle so as to be traversed by the plunger, and provided with a fitting structure matching that of the adapter of the syringe body, said tubular adapter and sleeve being of forms adapted to be able to penetrate one into the other so as to come into an interlocked position where their fitting structures cooperate, the protective case presents a diameter adapted to be able to slide externally along the syringe body, with a locking section able to cap the tubular adapter and the sleeve of the syringe body and handle, and to lock them in their fitted position, the protective case and the syringe body are provided with stop means adapted to define two end positions-a forward position where the case completely covers the needle and the base, and a rear position where at least the active portion of the needle is exposed and where the locking section of the case caps the fitted tubular adapter and sleeve of the syringe body and handle, so as to ensure locking of the syringe body/syringe handle union.

The manipulations required for the assembly and disassembly of this syringe are notably simplified as against the known dental syringes. In fact, the assembly of the syringe body and of the handle requires only a simple fitting, later locked when the protective case slides rearward. This case, therefore plays a dual role since, on the one hand, it ensures the protection of the practitioner against all risk of pricking before and after use and, on the other hand, it permits a quick assembly of the syringe body on the handle, without any risk of accidental disassembly.

As to protection, the case protects firstly the needle during assembly of the syringe body on the handle. Further, when the case is made to slide forward, once the oral injection is made, the risks of pricking are zero because the needle is covered by moving this case from the syringe body toward the end of the needle. the syringe body/protective case assembly can then be discarded, the needle being again housed in this protective case. It is noted, therefore, that the practitioner runs no risk of pricking whatever may be the operation carried out.

As to locking, the protective case will enclose the fitted tubular adapter and sleeve of the syringe body and of the handle and thus permits transforming this simple fitting into a rigid assembly without any risk of accidental disassembly. It should be noted, further, that when the case is brought to its forward position, the syringe body and the handle come apart automatically under the traction exerted on this case. Moreover, because the case ensures the locking of the fitting, the syringe body can no longer be disassembled and discarded without the needle being protected by this case.

Besides, the syringe body may have a threaded nose able to permit the screwing of a base provided with a tapped bore. However, this base is preferably sealed on the end of the syringe body. In fact, as the needle is initially sealed on its base, which itself is sealed on the end of the syringe body, the manipulations necessary for screwing this needle are thus eliminated.

Further, the syringe body and the protective case are preferably made of a transparent plastic material. Thus, the practitioner can see the level of liquid remaining in the cartridge.

According to a preferred realization, the fitting structures of the adapter and of the sleeve of the syringe body and handle consist of an annular rib and an annular notch of matching forms, formed so as to cooperate in the fitted position of said adapter and sleeve.

Besides its simplicity, this fitting systems, while blocking the syringe body and the handle in translatory direction, permits imparting to this assembly a degree of freedom in rotation. This arrangement enables the practitioner to orient the needle very easily so as to dispose the bevel of the needle appropriately during the injection.

Besides, the stop means are preferably formed by two external annular notches, referred to as front and back stop, on the syringe body, and by an internal annular rib in the protective case.

Further, according to another characteristic of the invention, the syringe has an annular blocking notch on the syringe body between the base and the front stop notch, said blocking notch presenting a rectangular cross-section matching that of the rib of the protective case and being adapted to provent any displacement of said case when said rib is lodged inside this blocking notch.

This blocking notch, in which the rib of the protective case will fit when the latter is made to slide forward, ensures against any subsequent reuse of the syringe body or against any accidental pricking when this syringe body is handled after it has been discarded.

The invention extends, as an essential structural element of this syringe, firstly, to an injection assembly for single use comprising:

a syringe body provided, at one of its ends, with a base carrying an injection needle so as to define an active injection portion, and at its opposite end, with a tubular adapter having a fitting structure, a protective case of a diameter adapted to be able to slide externally along the syringe body, with a locking section able to cap the tubular adapter of said syringe body, stop means on the protective case and the syringe body adapted to define two end positions—a forward position where the case completely covers the needle and the base, and a rear position where at least the active portion of the needle is exposed and where the locking section of the case caps the tubular adapter of the syringe body.

This invention extends also, as an essential structural element of the syringe, to a syringe handle comprising:

a finger-hold piece with a sleeve provided with a fitting structure, a movable plunger inside the support piece of the sleeve.

The invention extends also to a consumable module for single use for dentistry comprising in combination:

an injection assembly as described above, with a syringe body and a protective case disposed in its forward position where it completely covers the needle and the base, a cartridge integrated in the interior of the syringe body, a sterilized packaging bag of said injection assembly.

The invention described in a general manner above will be better understood on reading the detailed description which follows with reference to the annexed drawings which represent, by way of non-limiting example, a preferred form of realization thereof. In these drawings, which form an integral part of the present description:

BRIEF DESCRIPTION OF THE DRAWINGS

FIG. 1A is a perspective view of the syringe handle according to the present invention, FIG. 1B is a perspective view of the syringe body according to the present invention, FIG. 1C is a perspective view of the protective case according to the present invention, FIG. 6 is a longitudinal section through a plane DD of the body of a syringe according to the invention, FIG. 7 is a transverse section through a plane EE of this syringe body, FIG. 8 is a transverse section thereof through a plane FF, FIGS. 9, 10, 11 are longitudinal sections of this syringe, before, during, and after injection, respectively.

DESCRIPTION OF THE PREFERRED EMBODIMENT

Figure 2:
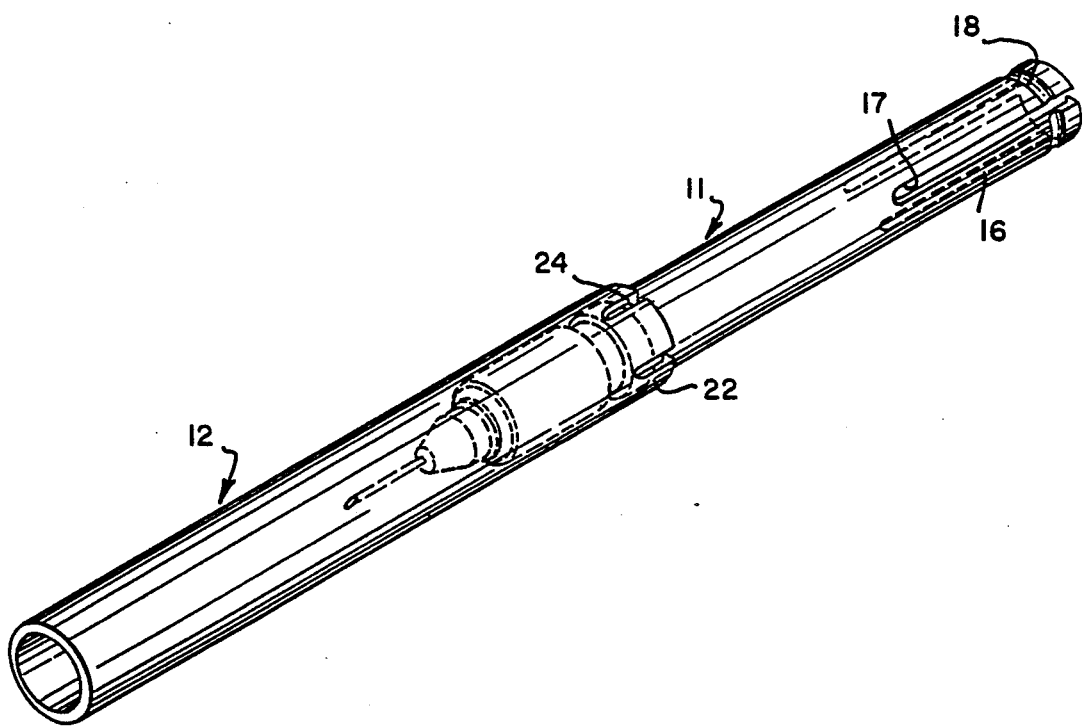
FIG. 2 is a perspective view of the assembly of protective case/syringe body, before assembly thereof.
Figure 3:
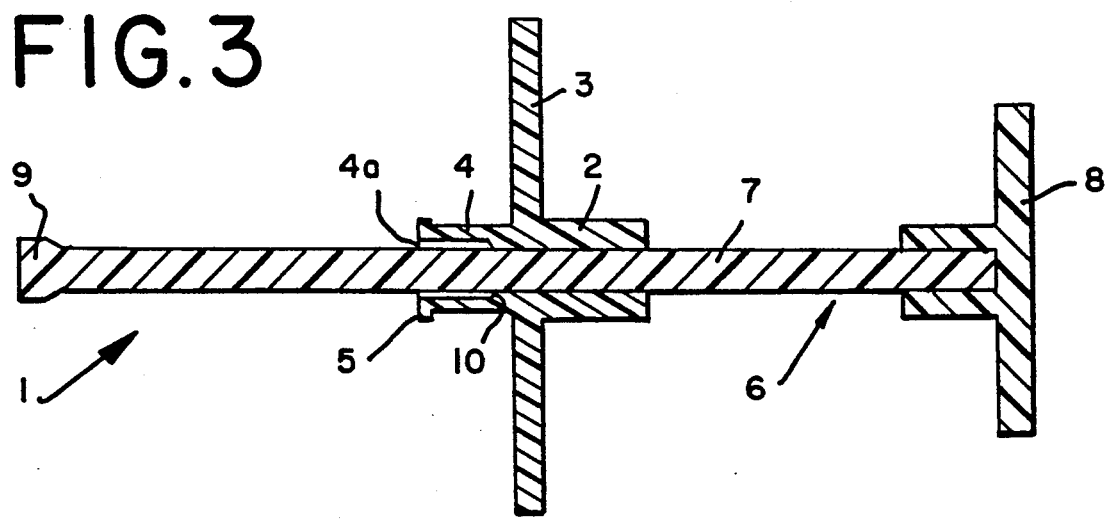
FIG. 3 is a longitudinal section through a plane AA of the handle of a syringe according to the invention.
Figure 4:
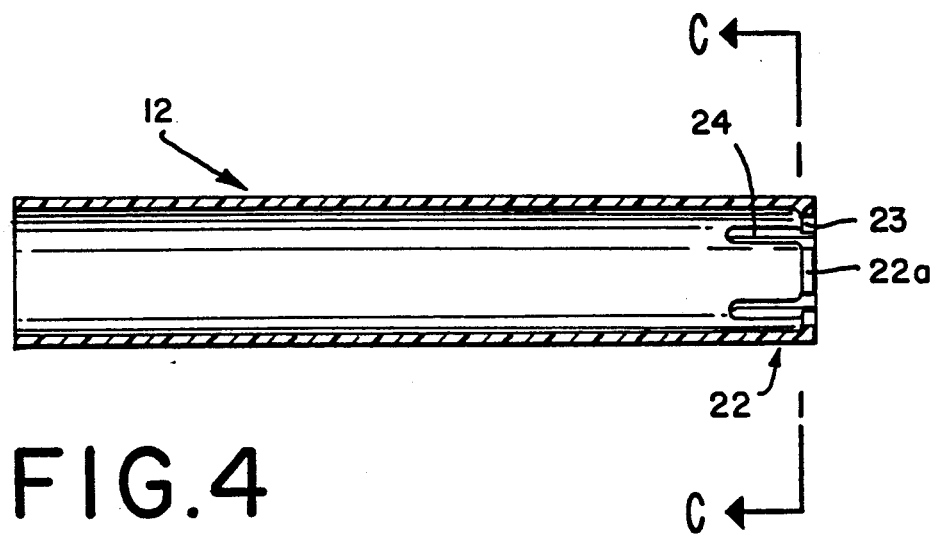
FIG. 4 is a longitudinal section through a plane BB of the protective case of a syringe accoording to the invention.
Figure 5:
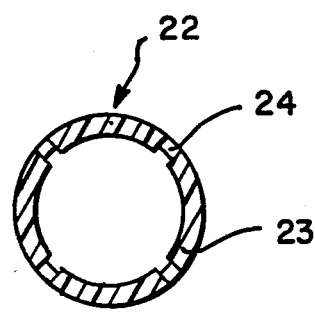
FIG. 5 is a transverse section through a plane CC of this protective case.

The syringe shown in the figures consists of three separate elements—a syringe body, a protective case, and a handle. The protective case and the syringe body are, moreover, adapted to be assembled, as represented in FIG. 2, so as to constitute a discardable injection assembly.

In the first place, the handle 1 of this syringe has a tubular support piece 2, with finger-grip ribs 3, and possessing, at one of its ends, a sleeve 4 ending in an open face 4a. This sleeve 4 has, furthermore, at the level of its open face 4a, an annular rib 5 on its outer peripheral face.

On the inside of the support piece 2, there is a maneuverable plunger 6 adapted to be able to slide inside this support piece and the sleeve 4. This plunger 6 has a rod 7 of a diameter substantially smaller than the inside diameter of the support piece 2. Said rod is provided at one of its ends with an operating button 8 which permits displacing the plunger 6 inside the support piece 2 of handle 1. It is provided at its opposite end with a collar 9 of a diameter greater than the diameter of this rod.

The immobility of this plunger 6 relative to the support piece 2 is obtained by means of an inner shoulder 10 in said support piece defining two sections of different inside diameter—a section of an inside diameter matching that of collar 9, ending at the open face 4a of sleeve 4, and a section of a diameter matching that of rod 7.

The second assembly of this syringe is composed of a syringe body 11 provided with a protective case 12 adapted to slide along this syringe body 11.

This syringe body 11 and this protective case 12 are made of a transparent plastic material permitting to see the level of the cartridge.

The syringe body 11, of a cylindrical general form, is provided at one of its ends with a sealed base 14 carrying an injection needle 15, so as to define an active injection portion. This syringe body 11 has, moreover, at its opposite end, a tubular adapter 16 ending in an open face 16a of an inside diameter adapted to house the sleeve 4 of handle 1.

This tubular adapter 16 has a plurality of longitudinal slots 17 (3 in the example) extending from its open face 16a, so as to permit its radial expansion when this adapter 16 comes in contact with the rib 5 of sleeve 4 of handle 1.

This tubular adapter 16 has, furthermore, an annular notch 18 of flared form provided on its outer peripheral face away from its open end 16a. It has also an inner annular notch 19 provided so as to cooperate with the rib 5 of sleeve 4 of handle 1, when the sleeve is lodged inside this adapter 16.

In addition, this syringe body 11 has two other annular notches 20, 21 provided on its peripheral face between the adapter 16 and the base 14—an annular blocking notch 20 of rectangular cross-section, provided at a certain distance from the base 14, and an annular notch 21 of flared cross-section provided between the blocking notch 20 cited above and the tubular adapter 16.

Lastly, this syringe body 11 comprises an inner rib 13 provided inside the tubular adapter 16, on the side of base 14 relative to the annular notch 19 of said adapter, said rib presenting an asymmetrical form adapted to permit the introduction of a cartridge 26 into the syringe body 11 and to prevent the withdrawal of this cartridge.

The protective case 12, in turn, presents a cylindrical form and has an inside diameter corresponding to the outside diameter of the syringe body 11.

The protective case 12 has a rear locking section 22 ending in an open face 22a and having, at the level of this open face 22a, an inner annular rib 23 of a form adapted to fit into the outer annular notches 18, 20, 21 of the syringe body 11.

This rear locking section 22 has lastly a plurality of longitudinal slots 24 (4 in the example) extending from its open face 22a and adapted to permit its radial expansion as rib 23 slides along the syringe body 11.

The use of this syringe is explained below with reference to FIGS. 9 to 12.

Figure 12:
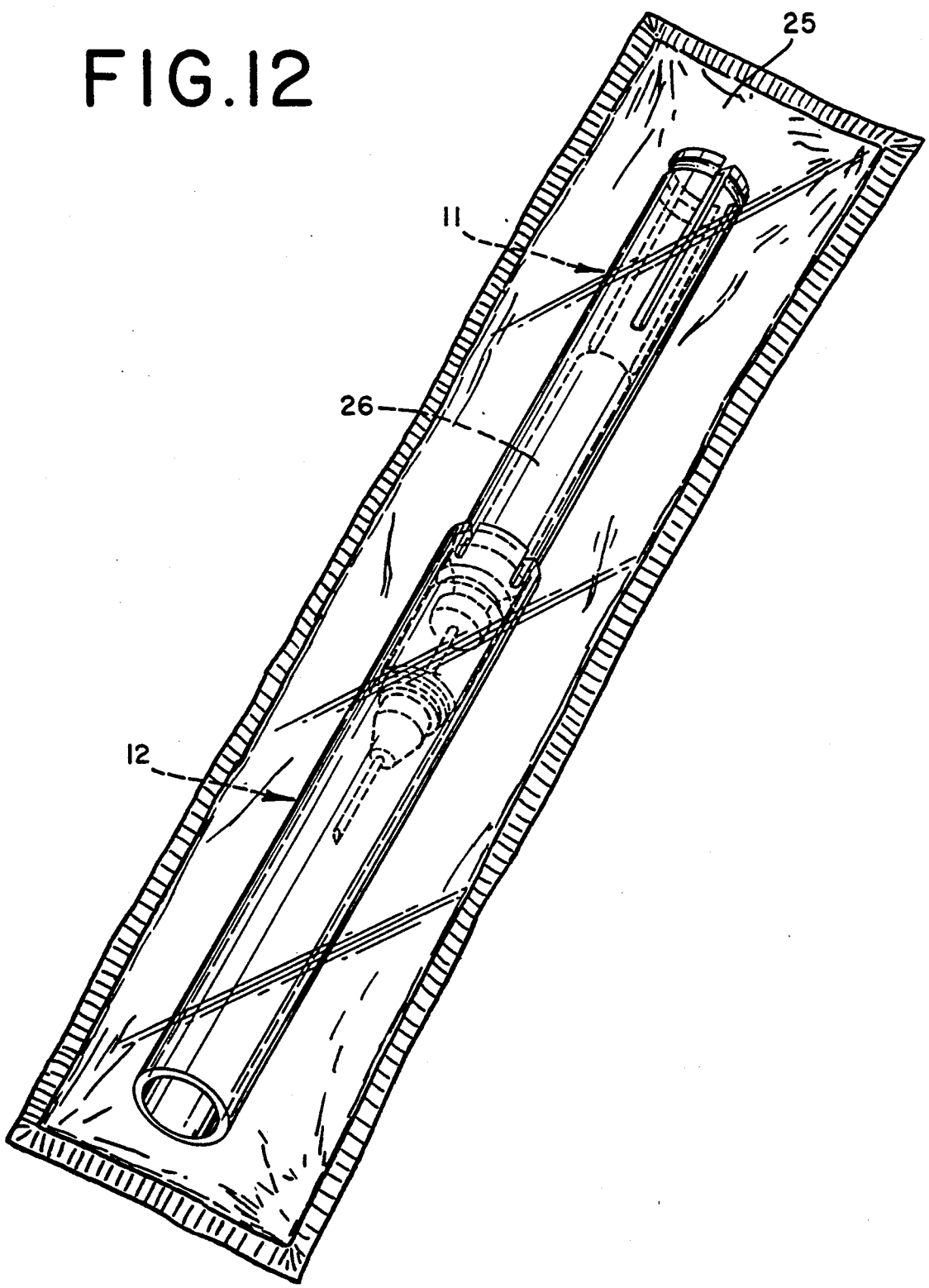
FIG. 12 is a perspective view of a consumable module for single use for a syringe according to the invention.

As shown in FIG. 12, the syringe body 11/protective case 12 assembly is packaged beforehand in a sterile bag 25, in a position where the inner rib 23 of the case is lodged in the flared front notch 21 of the syringe body 11. In this position, the protective case 12 completely covers the needle 15 and ensures against any risk of pricking or deterioration of this needle.

In addition, prior to the packaging, a cartridge 26 is introduced in the syringe body 11 in which it is held owing to the inner rib 13. It should be noted that this introduction is notably facilitated by the presence of slots 17 which permit a radial expansion of the tubular adapter 16. Thus a consumable module ready for use is obtained.

The injection assembly having been removed from its bag 25, sleeve 4 of handle 1 is inserted in the tubular adapter of the syringe body, in which it interlocks owing to the cooperation of the outer annular rib 5 and the inner annular notch 19 (FIG. 9).

The protective case 12 is then made to slide rearward until its inner annular rib 23 fits into the annular notch 18 of the tubular adapter 16 of the syringe body 11, in which position the active portion of needle 15 is exposed (FIG. 10).

In addition, in this position, the protective case 12 caps the tubular adapter 16 and the sleeve 4 of handle 1 and of the syringe body 11 and hence ensures the locking of the fitting.

Besides, during the injection, the practitioner can see the level of liquid remaining in the cartridge 26 without the patient being subjected to risks of its bursting.

At end of injection, the protective case 12 is made to slide forward until its inner rib 21 engages in the blocking notch 20 of the syringe body 11, after it has passed through the annular notch 21 of flared form. The traction exerted on this protective case 12 to bring about its sliding produces, moreover, automatically, the disengagement of the syringe body 11 and of the handle 1.

The assembly syringe body 11/protective case 12 can then be discarded, without risk of subsequent re-use or accidental pricking if this assembly is handled after having been discarded.

In addition, the form of rib 13 provents removing the cartridge 26 and ensures against any possible re-use thereof.

I claim:

1. Syringe of the type with an injection needle (15) for single use, notably for dentistry and comprising:
    a syringe handle (1) having a plunger (6) and a support piece (2, 3) traversed by said plunger and movable along the plunger,
    a syringe body (11) provided at one of its ends with a base (14) carrying the injection needle (15) so as to define an active injection portion,
    a removable attachment means (4, 5, 16, 19) for attaching the syringe body (11) to the syringe handle (1),
    and a protective case (12) of a form adapted to shield the needle (15) and its base (14), said syringe being characterized in that:
    the means for removable attachment comprises:
    a tubular adapter (16) engagable to the syringe body (11) opposite the base (14), and provided with a fitting structure (19),
    a sleeve (4) integral with the support piece (2, 3) of the handle (1) so as to be traversed by the plunger (6), and provided with a fitting structure (5) matching that of the tubular adapter (16) of the syringe body (11), said tubular adapter (16) and sleeve (4) being of forms adapted to be able to penetrate one into the other so as to come into a fitted position where their fitting structures (5, 19) cooperate,
    the protective case (12) is tubular and has a diameter adapted to be able to slide externally along the syringe body (11), with a locking section (22) able to cap the tubular adapter (16) and the sleeve (4) of the syringe body (11) and handle (1), and to lock them in their fitted position, the protective case (12) and the syringe body (11) are provided with stop means (18, 21, 23) adapted to define two end positions; a forward position where the case (12) completely covers the needle (15) and the base (14), and a rear position where at least the active portion of the needle (15) is exposed and where the locking section (22) of the case (12) caps the fitted tubular adapter (16) and sleeve (4) of the syringe body (11) and handle (1) so as to ensure a locking of the syringe body/syringe handle union.

2. Syringe according to claim 1 characterized in that it comprises a base (14) sealed on the end of the syringe body (11).

3. Syringe according to claim 1, in which the syringe body has a threaded nose able to permit the screwing on of a base provided with a tapped bore.

4. Syringe according to claim 1, characterized in that the fitting structures of the adapter (16) and sleeve (4) of the syringe body (11) and handle (1) consist of an annular rib (5) and an annular notch (19) of matching forms, arranged so as to cooperate in the fitted position of said adapter and sleeve.

5. Syringe according to claim 4, characterized in that the sleeve (4) of the syringe handle (1) is of a form adapted to penetrate into the adapter (16) of the syringe body (11), the annular rib (5) is on the sleeve (4) of the syringe handle (1), at the end thereof, the annular notch (19) is inside the adapter (16) of the syringe body (11), spaced from the end thereof, so as to obtain a fitted position in which the sleeve (4) of the handle (1) is engaged in the adapter (16) of the syringe body (11).

6. Syringe according to claim 5, characterized in that the adapter (16) of the syringe body (11) comprises an open end (16a) and a plurality of longitudinal slots (17) in said adapter extending to said open end (16a) so as to permit a radial deformation of said adapter.

7. Syringe according to claim 6, characterized in that the stop means for the protective case (12) consist of two outer annular notches (21, 18) called forward and rear stop notches respectively, said stops located on the syringe body (11), and of an inner annular rib (23), said rib extending from the protective case (12).

8. Syringe according to claim 7, characterized in that the annular rib (23) of the protective case (12) is at the end of the locking section (22) thereof, the rear stop notch (18) is at the end of the adapter (16) of the syringe body (11) so as to obtain a rear stop position of the protective case (12) in which the protective case caps the fitted tubular adapter (16) and sleeve (4), and the forward stop notch (21) is on the syringe body (11) at a distance from the base (14) adapted to obtain a forward stop position of the protective case (12) in which the protective case completely covers the needle (15) and said base (14).

9. Syringe according to claim 8, characterized in that the protective case (12) has a locking section (22) provided with a plurality of longitudinal slots (24) extending to its end (22a) so as to permit a radial deformation of said section.

10. Syringe according to claim 9, characterized in that it has an annular blocking notch (20), said annular blocking notch is on the syringe body (11) between the base (14) and the forward stop notch (21), said blocking notch having a rectangular cross section matching that of the rib (23) of the protective case (12) and being adapted to prevent any displacement of said protective case when said rib (23) is lodged inside this blocking notch (20).

11. Syringe according to claim 5, characterized in that it comprises an inner rib (13), said inner rib is inside the tubular adapter (16) of the syringe body (11), on the base side (14) relative to the annular notch (19) of said adapter, said rib having an asymmetrical form adapted to permit the introduction of a cartridge (26) into the syringe body (11) and to prevent the withdrawal of the cartridge.

12. Syringe according to claim 11, characterized in that it comprises a syringe body (11) and a protective case (12) made of a transparent plastic material, adapted to permit visualizing the level of liquid contained in the cartridge (26).

13. Single use injection assembly for a syringe, characterized in that it comprises:

a syringe handle (1) having a plunger (6) and a support piece (2, 3) traversed by said plunger, said plunger movable along said support piece, a removable attachment means (4, 5, 16, 19) for attaching the syringe body (11) to the syringe handle (1), a syringe body (11) provided, at one of its ends, with a base (14) carrying an injection needle (15) so as to define an active injection portion, and at its opposite end, a tubular adapter (16) having a fitting structure (19), a protective case (12) of a diameter adapted to be able to slide externally along the syringe body (11), with a locking section (22) able to cap the tubular adapter (16) of said syringe body, stop means on the protective case (12) and syringe body (11), adapted to define two end positions, a forward position, where the protective case (12) completely covers the needle (15) and the base (14), and a rear position, where at least the active portion of the needle (15) is exposed and where the locking section (22) of the protective case (12) caps the tubular adapter (16) of the syringe body (11).

14. Single use injection assembly for a syringe, according to claim 13, wherein said handle further comprises:

a finger support piece (2, 3) having a sleeve (4) provided with a fitting structure (5).

15. Single use injection assembly for a syringe according to claim 14, characterized in that the fitting structure of the sleeve (4) consists of an annular rib (5) at the end of said sleeve.

16. Single use injection assembly for a syringe according to claim 13, characterized in that it comprises in combination:

an injection assembly having a syringe body (11), and a protective case (12) disposed in its forward position where it covers the needle (15) and the base (14), a cartridge (26) integrated in the interior of the syringe body (11), a sterilized bag (25) for packaging said injection assembly.

17. Single use injection assembly for a syringe according to claim 16, characterized in that it comprises in combination:

the fitting structure of the tubular adapter (16) of the syringe body (11) is formed by an annular notch (19)

and where the syringe body (11) comprises an inner rib (13) inside the tubular adapter (16), on the base side (14) relative to the annular notch (19) of said adapter, said rib presenting an asymmetrical form adapted to permit the introduction of a cartridge (26) into the syringe body (11) and to prevent the withdrawal of said cartridge.

18. Injection assembly according to claim 13, characterized in that the fitting structure of the tubular adapter (16) of the syringe body (11) is formed by an annular notch (19).

19. Injection assembly according to claim 18, characterized in that the tubular adapter (16) at the syringe body (11) comprises an open end (16a) and a plurality of longitudinal slots (17) in said adapter extending to said open end (16a).

20. Injection assembly according to claim 19, characterized in that the stop means of the protective case (12) are formed by two external annular stop notches (21, 18) called forward and rear stop notches respectively, said stop notches on the syringe body (11), and by an inner annular rib (23) in the protective case (12).

21. Injection assembly according to claim 20, characterized in that:

the annular rib (23) of the protective case (12) is at the end of the locking section (22) of the protective case, the rear stop notch (18) is at the end of the adapter (16) of the syringe body (11) so as to obtain a rear stop position of the protective case (12) in which the protective case caps the tubular adapter (16) of the syringe body (11), and the forward stop notch (21) is on the syringe body (11) at a distance from the base (14) adapted to obtain a forward stop position of the protective case (12) in which the protective case completely covers the needle (15) and said base (14).

22. Injection assembly according to claim, 21 characterized in that the protective case (12) has a locking section (22) provided with an open end (22a) and a plurality of longitudinal slots (24) in said locking section extending to said open end (22a) so as to permit a radial deformation of said section.

23. Injection assembly according to claim 22, characterized in that the syringe body (11) has an annular blocking notch (20) between the base (14) and the forward stop notch (21), said blocking notch presenting a rectangular cross-section matching that of the annular rib (23) of the protective case (12) and being adapted to prevent any displacement of said case when said rib (23) is lodged inside this blcoking notch (20).

24. Injection assembly according to claim 23, characterized in that the syringe body (11) comprises an inner rib (13) inside the tubular adapter (16), on the base side (14) relative to the annular notch (19) of said adapter, said rib presenting an asymmetrical form adapted to permit the introduction of a cartridge (26) into the syringe body (11) and to prevent the withdrawal of this cartridge.

25. Injection assembly according to claim 24, characterized in that it comprises a syringe body (11) and a protective case (12) made of a transparent plastic material adapted to permit visualizing the level of liquid contained in the cartridge (26).

26. Injection assembly according to claim 25, characterized in that it comprises a base (14) sealed on the end of the syringe body (11).

27. Injection assembly according to claim 25, in which the syringe body has a threaded nose able to permit the screwing on of a base (14) provided with a tapped bore.

* * * * *